(12) United States Patent
Anderson

(10) Patent No.: US 7,775,938 B1
(45) Date of Patent: Aug. 17, 2010

(54) EXERCISER FOR MUSCLES THAT PROTRACT AND DEPRESS THE MANDIBLE

(76) Inventor: Daniel Thomas Anderson, P.O. Box 1526, Rogue River, OR (US) 97537

( * ) Notice: Subject to any disclaimer, the term of this patent is extended or adjusted under 35 U.S.C. 154(b) by 116 days.

(21) Appl. No.: 12/378,776

(22) Filed: Feb. 18, 2009

(51) Int. Cl.
A63B 21/03 (2006.01)

(52) U.S. Cl. ............................ 482/11; 482/121; 482/10

(58) Field of Classification Search ................... 482/10, 482/11; 128/848
See application file for complete search history.

(56) References Cited

U.S. PATENT DOCUMENTS

| 1,587,558 | A | * | 6/1926 | Sheffield | 128/848 |
| 4,650,182 | A | | 3/1987 | Ross | |
| 4,658,811 | A | * | 4/1987 | Beaird | 606/204.35 |
| 4,694,823 | A | | 9/1987 | Young | |
| 5,484,359 | A | | 1/1996 | Wabafiyebazu | |
| 5,893,365 | A | | 4/1999 | Anderson | |
| 6,016,807 | A | | 1/2000 | Lodge | |
| 7,121,824 | B2 | | 10/2006 | Keles et al. | |
| 7,225,811 | B2 | | 6/2007 | Ruiz et al. | |
| D550,849 | S | | 9/2007 | Baker | |
| 2006/0106330 | A1 | | 5/2006 | Andrade et al. | |
| 2007/0181135 | A1 | * | 8/2007 | Baker | 128/848 |

* cited by examiner

Primary Examiner—Jerome Donnelly
(74) Attorney, Agent, or Firm—Holland & Hart LLP

(57) ABSTRACT

An exerciser for muscles that protract and depress the mandible. A headpiece is adapted to fit around an upper rearward portion of a human head. A chin strap extends around the chin and is coupled to the headpiece at such an angle that the chinstrap is urged against the chin in opposition to both protraction and depression of the chin. The exerciser finds an application in treating temporomandibular joint dysfunction (TMD).

10 Claims, 6 Drawing Sheets

EXERCISER FOR MUSCLES THAT PROTRACT AND DEPRESS THE MANDIBLE

BACKGROUND

The temporomandibular joint (jawbone joint, or TMJ for short) is a modified hinge joint connecting the condylar head of the mandible to the temporal bone of the skull. Opening and closing the mouth or jaw is a combination of translatory (i.e., gliding) and rotational movements of the condylar head along the temporal bone. Translation of the condylar head produces protrusion (protraction) of the chin and retrusion (retraction) of the chin. Rotation of the condylar head produces depression and elevation of the mandible. The primary muscle involved in protrusion is the lateral pterygoid muscle. The primary muscle responsible for retrusion is the temporal muscle with minimal, secondary involvement of the masseter muscle. Along with gravity, the muscles responsible for depression or opening the jaw are the lateral pterygoid muscle and the small, strap like muscles located at the front of the neck called the supra and infra hyoid muscles. The primary muscles responsible for elevation or closing the jaw and opposing the hyoid muscle group are the larger and more dominating temporal, masseter and medial pterygoid muscles located at the sides of the skull and jaw.

The temporal, masseter and medial pterygoid muscles that close the mouth work almost constantly in such activities as chewing, talking, and stressful clenching. As a result, these muscles can become overly strengthened and shortened with respect to the supra hyoid, infra hyoid and lateral pterygoid muscles that open the mouth. This creates an imbalance at the TMJ. Poor alignment of the head and neck worsens this imbalance, and both the TMJ imbalance and the neck musculature imbalance may perpetuate each other's dysfunction. Such imbalance results in discomfort and pain that can lead to tinnitus, vertigo, headache, vision problems, difficulties in chewing and talking, and pain in the upper back and shoulders. This condition is known as TMJ dysfunction (TMD). TMD can be self-perpetuating in that the muscles that close the mouth go into spasms, resulting in more clenching that aggravates the condition.

Physical therapy and rehabilitation using exercise are based on restoring normal function and balance within the musculoskeletal system. Each skeletal muscle or agonist has at least one opposing or antagonistic muscle with which it interacts. The proportional strength ratio of antagonistic to agonist muscle pairs must be in balance for muscles to function normally. Imbalances can occur from inactivity, overuse, disease, malnutrition and direct trauma resulting in injury. To restore balance, a therapist must identify the muscles that have become dysfunctional and determine which ones are weak versus those of their antagonists that have become over dominating. By designing an exercise regime that strengthens the weak muscles and therefore lessens the influence of the over dominating muscles, balance is restored and normal, pain free function is re-established.

Therapeutic exercises for restoring normal function to target muscles and the joints they act upon stimulate (activate) target muscles and in turn stretch their antagonistic partners. Therapeutic exercise for TMD is designed to stimulate the muscles that open and protrude the jaw and in turn stretch the antagonistic muscles that close and retract the jaw. The muscles and the joint they act upon should be exercised through their full functional range of motion. Therefore, the exercise should ensure the rotational and translatory motion aspects of the TMJ throughout the applied resistance.

Patients with TMD are often instructed to apply their hand or fist to their chin to generate resistance against opening and protracting the jaw. This strengthens the lateral pterygoid and hyoid muscles, alleviating the imbalance at the TMJ. However, applying resistance in this manner creates counterproductive tension in the musculature of the arms, shoulders or neck and induces poor head position. This tension limits the effectiveness of the exercise.

A variety of devices generally fitting the head and neck have been described. U.S. Publication 2006/0,106,330 to Andrade et al. depicts a facial toning device. U.S. Pat. No. 4,694,823 to Young shows a neck and facial lifter. Anti-apnea appliances are described in U.S. Pat. No. 5,893,365 to Anderson; U.S. Pat. No. 7,225,811 to Ruiz et al.; U.S. Publication 2007/0,181,135 to Baker; and U.S. Pat. No. D550,849 to Baker. U.S. Pat. No. 5,484,359 to Wabafiyebazu shows a full-face enclosure for toning chin muscles. An orthodontal device is shown in U.S. Pat. No. 7,121,824 to Keles et al. A device for tensioning the TMJ as treatment for a dislocated jaw is shown in U.S. Pat. No. 6,016,807 to Lodge. U.S. Pat. No. 1,587,558 to Sheffield illustrates a jaw bracing and setting device with a fixed angle between a chin strap and a head strap assembly. A jaw exercising device also with a fixed angle between chin strap and headband is disclosed in U.S. Pat. No. 4,650,182 to Ross.

There remains a need for a way to strengthen the lateral pterygoid and hyoid muscles so as to alleviate TMD without undesirable effects on musculature elsewhere in the human body.

SUMMARY OF THE INVENTION

The invention resides in an exerciser for muscles that protract and depress the mandible. In one aspect an embodiment of the invention has a headpiece adapted to fit around an upper rearward portion of a human head. A chin strap is adapted to extend around a human chin. A first extremity of the chin strap is coupled to a first extremity of the headpiece and a second extremity of the chin strap is coupled to a second extremity of the headpiece. The chin strap is coupled to the headpiece at such an angle that the chin strap is urged against the chin in opposition to both protrusion and depression of the chin.

Other aspects of the invention will become apparent from the following detailed description and the accompanying drawings, illustrating by example the principles of the invention.

DESCRIPTION OF THE EMBODIMENTS

Figure 1:
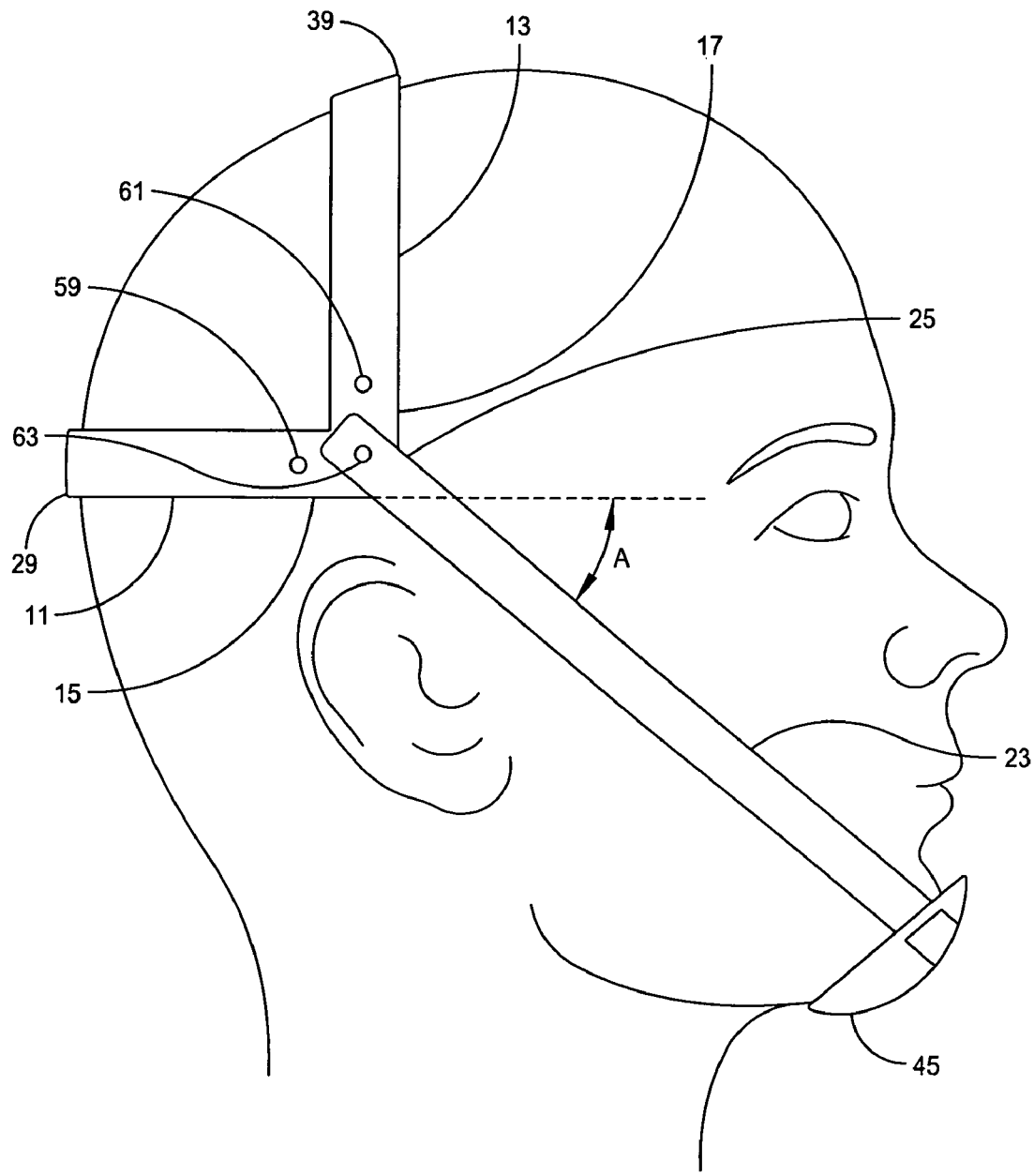
FIG. 1 is a perspective view of an exercise embodying the invention, fitted to a human head.
Figure 2:
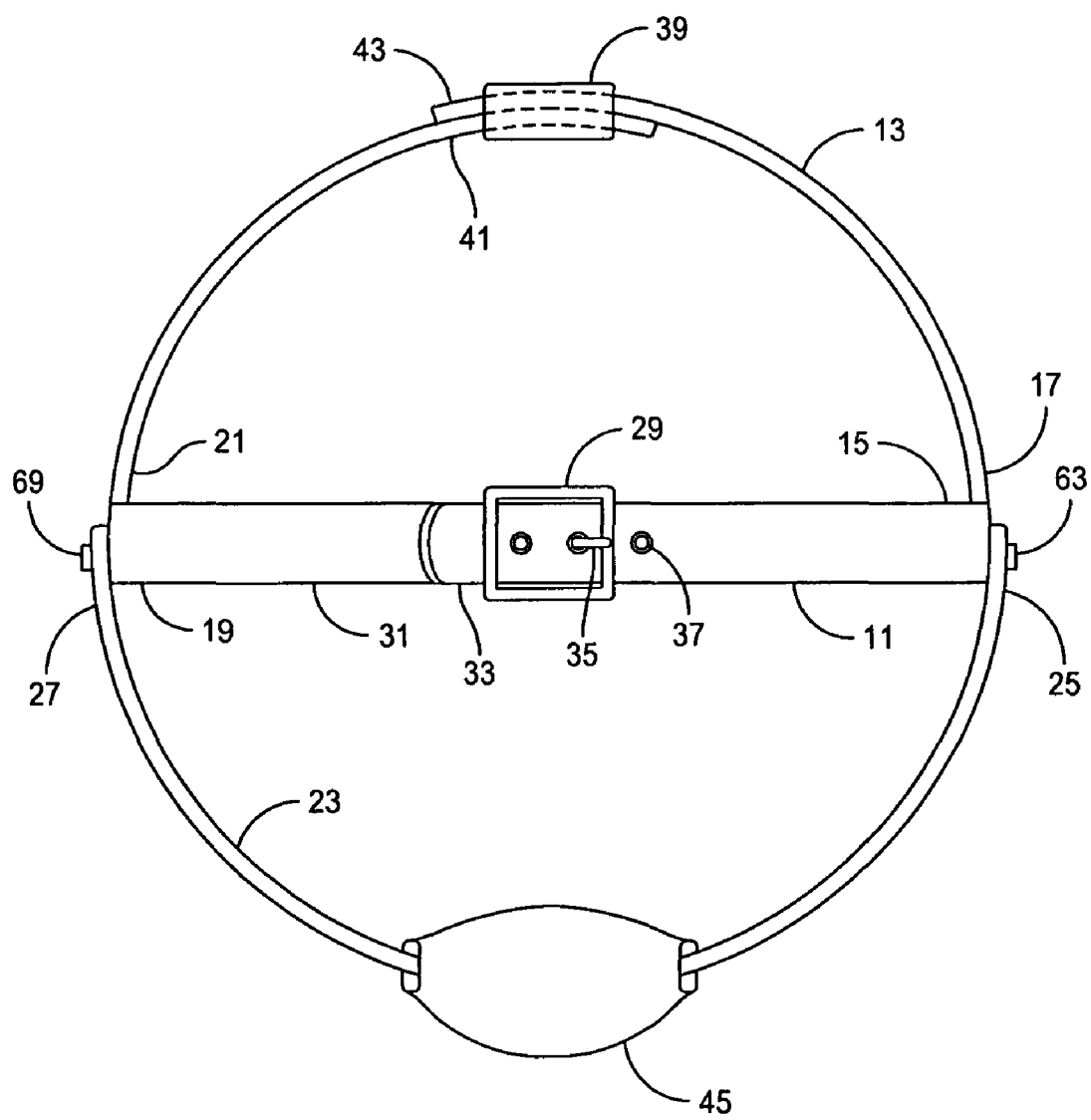
FIG. 2 is a rear view of the exerciser of FIG. 1, illustrating a horizontal strap and chin strap.

An exerciser for muscles that protract and depress the mandible according to an embodiment of the invention is shown in FIGS. 1 and 2. A headpiece is adapted to fit around an upper rearward portion of a human head. In the embodiment shown, the headpiece includes a horizontal headband 11 adapted to extend around the rear of the head in an approximately horizontal orientation and a vertical headband 13 adapted to extend around the upper part of the head in an approximately vertical orientation. The horizontal and vertical headbands may be formed of a single piece of material or may be formed as two separate straps that are coupled together at the extremities. In other embodiments (not shown) the headpiece may be shaped differently, for example as a single concave surface that fits the upper rear part of the head.

An elastic chin strap 23 is adapted to extend around a human chin. A coupler (to be described in more detail presently) connects a first extremity 25 of the chin strap to a first extremity of the headpiece. In the embodiment shown, the first extremity of the headpiece includes first extremities 15 and 17 of the vertical and horizontal headbands. Likewise, a second extremity 27 of the chin strap is coupled to second extremities 19 and 21 of the vertical and horizontal headbands.

The chin strap is coupled to the headbands at such an angle that the chinstrap is urged against the chin in opposition to both protrusion and depression of the chin. As shown in FIG. 1, the angle A between the chin strap 23 and the horizontal headband 11 must be small enough that the chin strap resists protrusion as well as depression. If angle A is too large, the chin strap resists mainly depression and does not resist protraction sufficiently to achieve the desired therapeutic treatment. Of course, if angle A is too small the chin strap does not resist depression enough. When the exerciser is fitted to a given patient, the connection of the chin strap to the headbands is adjusted such that the angle A provides optimal resistance to both protrusion and depression. In some embodiments the angle is adjustable from about 40 degrees to about 60 degrees, and in other embodiments the angle is adjustable to as low as about 20 degrees or as high as about 80 degrees.

The horizontal headband 11 may include an adjustment buckle 29. The adjustment buckle may adjustably couple first and second portions 31 and 33 of the horizontal headband such that the horizontal band can be adjusted, for example by inserting a tongue 35 into any of a plurality of buckle holes 37 formed in the second portion 33 of the horizontal headband. The vertical headband 13 may include a similar adjustment buckle 39 that adjustably couples first and second portions 41 and 43 of the vertical headband.

The first extremity 15 of the horizontal headband may be joined to the first extremity 17 of the vertical headband by any convenient attachment means. Or the horizontal and vertical headbands may be formed from a single piece of material, as will be described in more detail presently.

Figure 3:
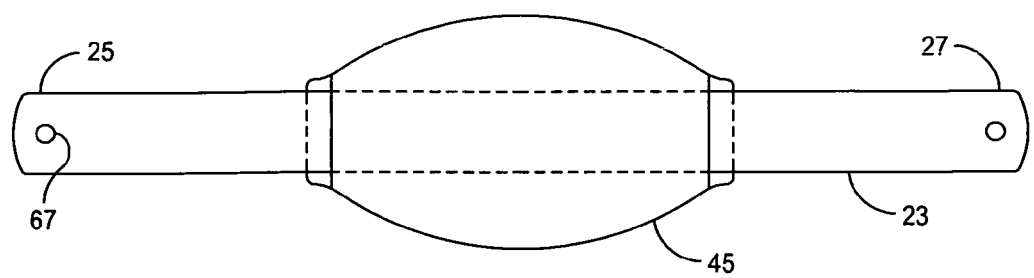
FIG. 3 is a view of a chin strap that can be used in an exerciser embodying the invention.
Figure 4:
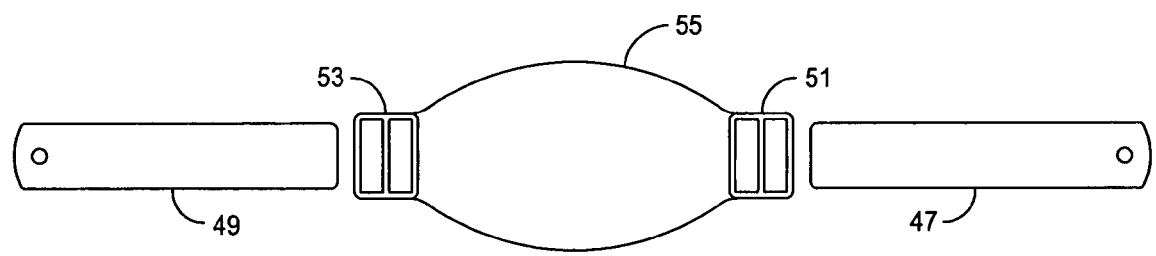
FIG. 4 is a view of another chin strap that can be used in an exerciser embodying the invention.
Figure 5:
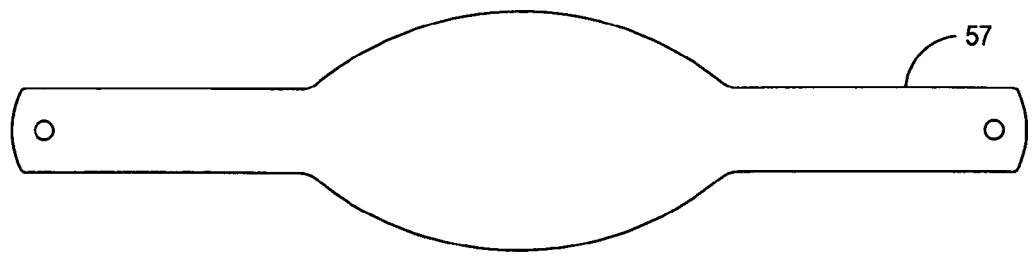
FIG. 5 is a view of another chin strap that can be used in an exerciser embodying the invention.

The chin strap 23 may include an elongated strip and a chin cup 45 slidingly carried by the strip, as shown in FIG. 3. Or the chin strap may be made of a pair of elongated strips 47 and 49 looped through couplers 51 and 53 of a chin cup 55, as shown in FIG. 4. An adjustment buckle similar to the buckle 29 of the horizontal headband may be included in the chin strap if desired. The chin cup may be shaped such that any slots or buckles extend away from the chin so as to hold the chin strips away from the skin of the cheeks. In another embodiment, the chin cup and elongated strip may be formed from a single piece of material 57 as shown in FIG. 5.

Figure 6:
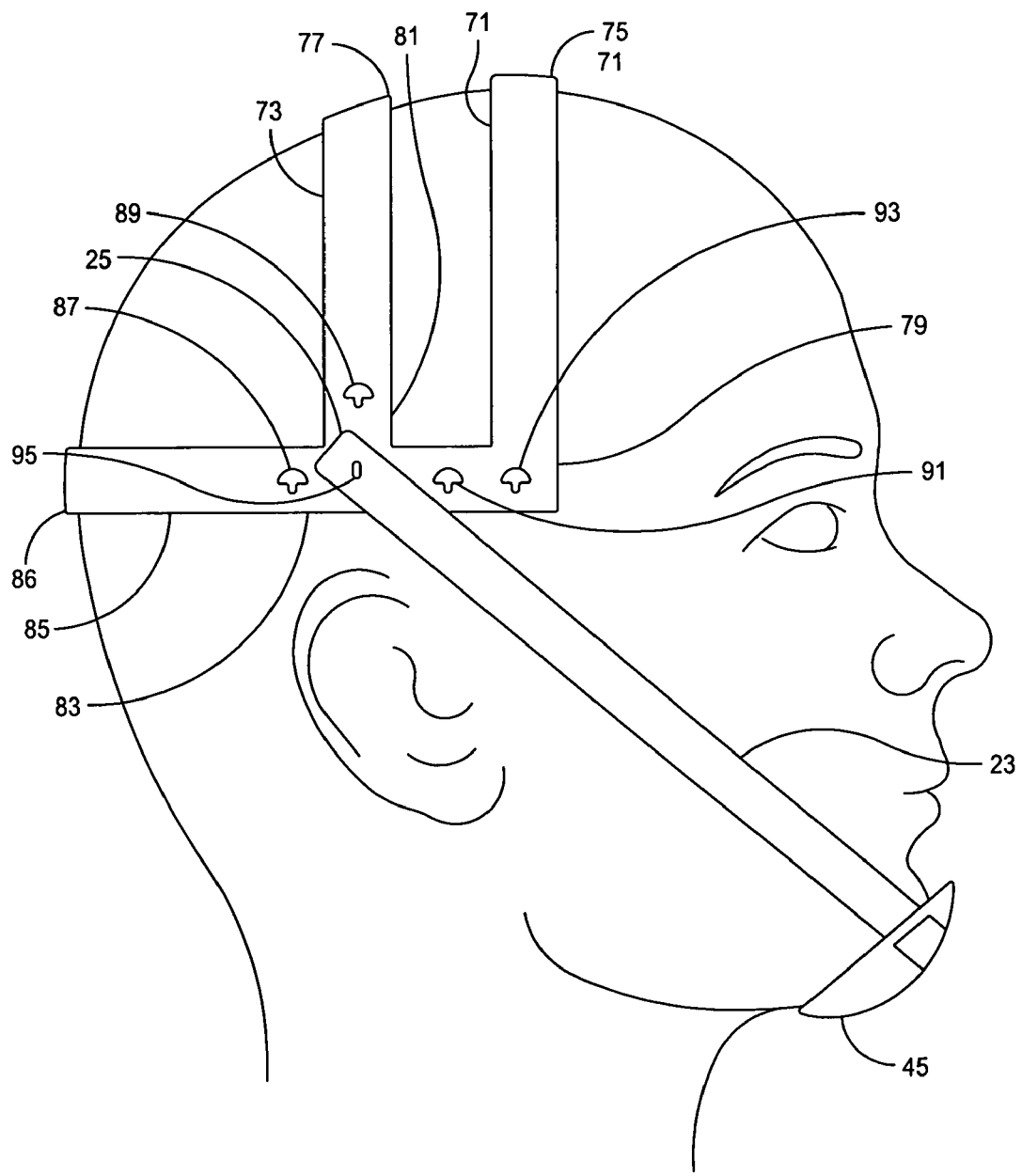
FIG. 6 is a perspective view of another embodiment of an exerciser embodying the invention.

The coupler may include a plurality of connection points formed in one or both of the first extremities of the horizontal headband and the vertical headband. The chin strap may be connected to any of these connection points so as to obtain appropriate tension on the chin strap and so as to set the angle between the chin strap and the headbands such that the chin strap is urged against the chin in opposition to both protrusion and depression of the chin. As shown in the drawings, the connection points may be above and behind the ear. For example, the connection point 59 in FIG. 1 and the connection point 87 in FIG. 6 are above and behind the ear. Some embodiments include a plurality of connection points above and behind the ear extending toward the region of the buckle 29 so the chin strap can be connected at a suitable angle (angle A in FIG. 1) to resist both protrusion and depression of the chin. As noted above, in some embodiments the connection points are located such that a desired angle between about 40 degrees and 60 degrees can be selected, for example in five-degree or ten-degree increments. More connection points are provided in some embodiments to permit the angle to be set as low as about 20 degrees or as high as about 80 degrees. An exerciser having a variety of connection points that permit selection of many different angles offers the flexibility of being adjustable to meet a wide range of patient needs.

For example, a connection point 59 may be formed in the first extremity 15 of the horizontal headband 11 and a connection point 61 may be formed in the first extremity 17 of the vertical headband 13. The connection point may take the form of a receptacle adapted to receive a connector carried by the chin strap. As shown in FIG. 1, a connector such as a pin 63 carried by the chin strap 23 has been inserted into a receptacle (concealed beneath the chin strap) similar to the connection points 59 and 61.

In another embodiment the connection points 59 and 61 may take the form of protrusions such as pins or hooks, and the first extremity 25 of the chin strap 23 may have a hole 67 (shown in FIG. 3) adapted to fit over one of these protrusions.

Similarly, the second extremity 27 of the chin strap is coupled to the second extremities 19 and 21 of the horizontal and vertical headbands, for example by a pin 69.

As shown in FIG. 6, in some embodiments the vertical headband comprises a forward band 71 and a rearward band 73. The forward band 71 may include an adjustment buckle 75 similar to the adjustment buckle 39, and the rearward band 73 may include an adjustment buckle 77. A first extremity 79 of the forward band 71 and a first extremity 81 of the rearward band 73 are joined to a first extremity 83 of a horizontal headband 85 having a buckle 86, or all three bands may be formed from a single piece of material.

Figure 7:
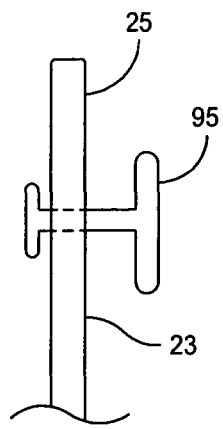
FIG. 7 is a view of a connector pin that can be used in an exerciser embodying the invention.

A plurality of connection points 87, 89, 91, and 93 are carried by the extremities 79, 81 and 83 of the forward, rearward and horizontal bands. As shown in detail in FIG. 7, these connection points may be shaped to receive a rivet-shaped connector 95 carried by the first extremity 25 of the chin strap 23, or any of the other connectors previously described may be used.

Figure 8:
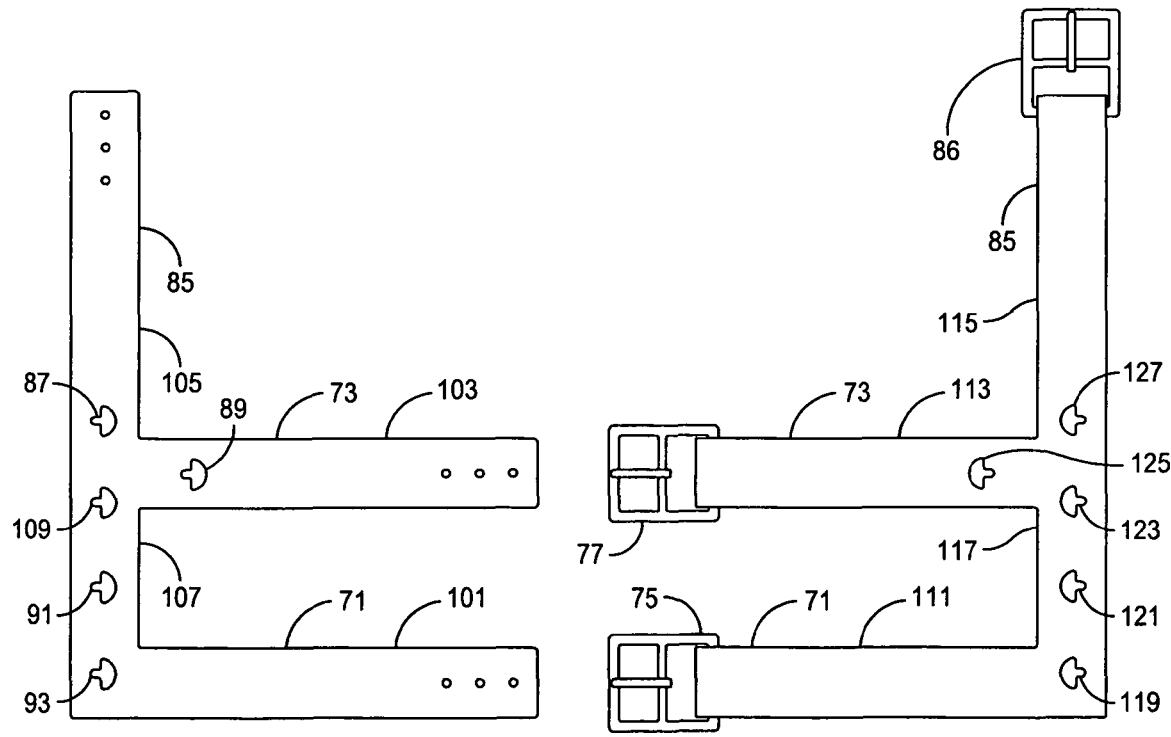
FIG. 8 illustrates one way to make some of the parts of the exerciser of FIG. 6.

The forward, rearward, and horizontal bands may be integrally made. For example, as shown in FIG. 8 a first portion 101 of the forward band 71, a first portion 103 of the rearward band 73, and a first portion 105 of the horizontal band 85 may be formed of a single piece of material. This material may be cut such that each of the three bands is about 1.9 to 2.5 centimeters (0.75 to 1.0 inches) in width, and the three bands are joined together by a center section 107 in which the receptacles 91 and 93 are formed. Also in the center section is a receptacle 109. The receptacle 109 is concealed from view in FIG. 6 behind the connector 95 which has been inserted into the receptacle 109.

A similar construction may be used for the second portions 111, 113 and 115 of the three bands 71, 73 and 85, the second portions of the bands being joined by a center section 117. Receptacles 119, 121, 123, 125 and 127 are provided.

In other embodiments some or all of the three bands may be formed of separate pieces and then glued or otherwise attached together. Or in still other embodiments, the entire assembly of forward, rearward and horizontal bands 71, 73 and 85 may be formed of a single piece of elastic material that stretches to fit as it is placed over the head.

The receptacles may comprise slots. In other embodiments (not shown) the connector may take the form of a receptacle formed in the first extremity 25 of the chin strap and a plurality of pins carried by the center section 107.

The bands may be lined with padding material (not shown) for greater comfort in wearing the exerciser. When buckled or otherwise connected, the three bands span the circumference of the skull, approximately from one temporomandibular joint (TMJ) to the other.

Figure 9:
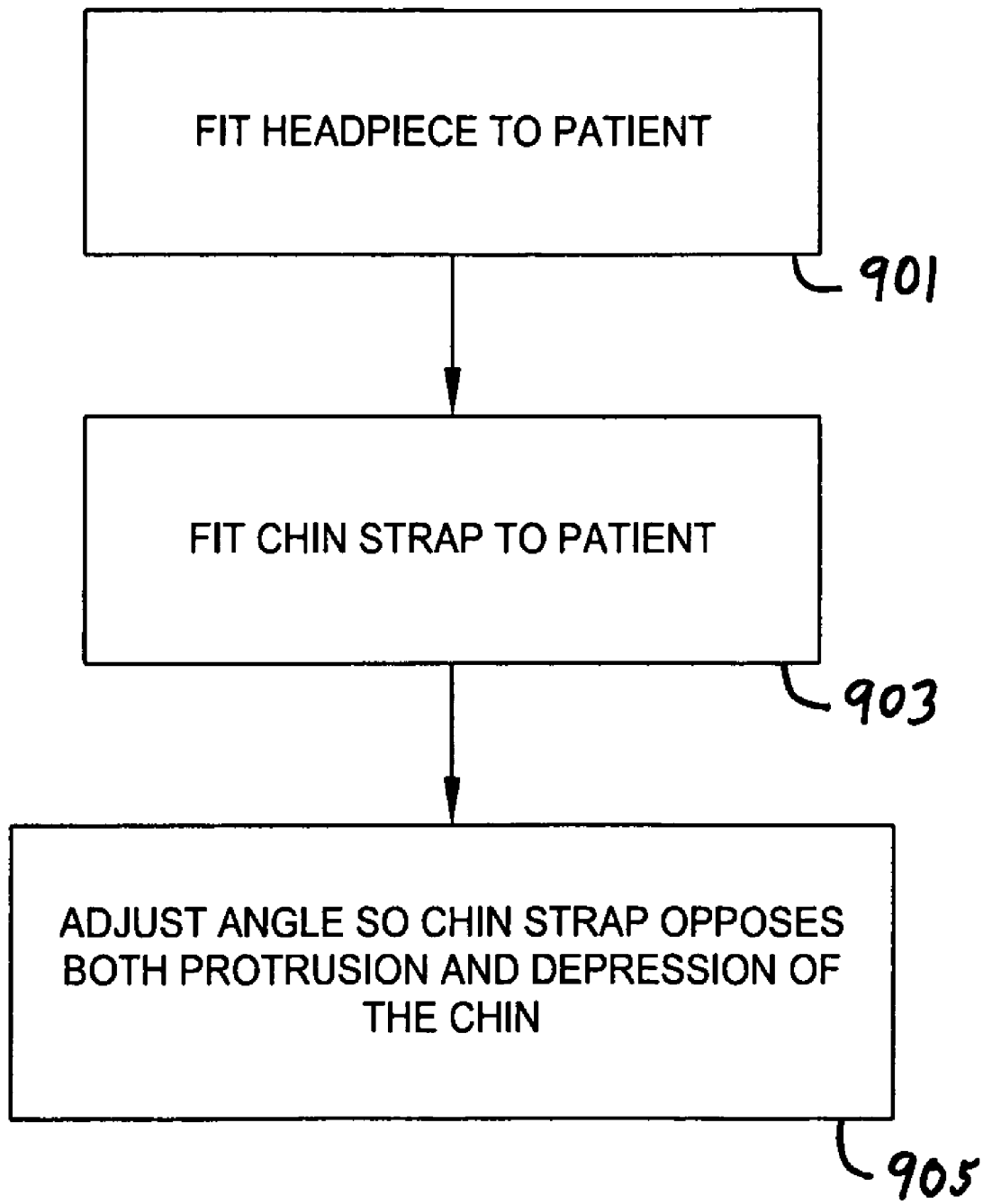
FIG. 9 illustrates a method of treating TMD according to the invention.

As shown in FIG. 9, the invention provides a method of treating temporomandibular joint dysfunction (TMD). A headpiece is fitted (901) to a patient suffering from TMD. A chin strap carried by the headpiece is fitted (903) to the chin of the patient. An angle between the chin strap and the headpiece is adjusted (905) to urge the chin strap against the chin in opposition to both protraction and depression of the chin.

An exerciser as described above resists the mandible as a patient uses the infra and supra hyoid muscles and the lateral pterygoid muscle to open the mouth (depress the mandible) and stick the chin out (protract the mandible). The method described above adjusts an angle between chin strap and headpiece to resist protrusion and depression of the mandible. This resistance to both motions stimulates and strengthens these muscles. These muscles are antagonistic to the temporal, masseter and medial pterygoid muscles that raise the mandible (close the mouth). As the hyoid and lateral pterygoid muscles grow stronger, the temporalis, masseter and medial pterygoid muscles gradually lengthen, restoring balance within the TMJ complex and alleviating TMD. The plurality of connection points between the chin strap and the horizontal and vertical headbands, including in some embodiments connection points above and behind the ear, allows the equalizer to be adjusted for an appropriate amount of resistance to each of depression and protraction for optimal treatment of each patient.

The invention may be implemented otherwise than in the embodiments as described above. Accordingly, the scope of the invention is to be limited only by the claims.

I claim:

1. An exerciser for muscles that protract and depress the mandible comprising:
    a first strap having forward and intermediate extremities generally parallel each other and a rearward extremity generally at right angles to the forward and intermediate extremities;
    a second strap having forward and intermediate extremities generally parallel each other and a rearward extremity generally at right angles to the forward and intermediate extremities;
    complementary couplers carried by the forward extremity of the first strap and the forward extremity of the second strap whereby the forward extremities of the two straps can be coupled together to define a forward band for fitting over a human head in a generally vertical orientation;
    complementary couplers carried by the intermediate extremity of the first strap and the intermediate extremity of the second strap whereby the intermediate extremities of the two straps can be coupled together to define an intermediate band for fitting over a human head generally parallel the forward band and spaced apart therefrom;
    complementary couplers carried by the rearward extremity of the first strap and the rearward extremity of the second strap whereby the rearward extremities of the two straps can be coupled together to define a rearward band for fitting over a human head in a generally horizontal orientation; and
    an elastic chin strap adapted to extend around a human chin and connectable to the first and second straps at such an angle that the chinstrap is urged against the chin in opposition to both protraction and depression of the chin.

2. An exerciser as in claim 1 wherein the complementary couplers carried by the forward extremities comprise an adjustment buckle and mating receiver whereby the forward band can be adjusted to fit a human head.

3. An exerciser as in claim 1 wherein the complementary couplers carried by the intermediate extremities comprise an adjustment buckle and mating receiver whereby the intermediate band can be adjusted to fit a human head.

4. An exerciser as in claim 1 wherein the complementary couplers carried by the rearward extremities comprise an adjustment buckle and mating receiver whereby the rearward member can be adjusted to fit a human head.

5. An exerciser as in claim 1 wherein the chin strap comprises an elongated strip and a chin cup slidingly carried by the strip.

6. An exerciser as in claim 1 wherein the chin strap comprises a pair of elongated strips and a chin cup, a first extremity of each elongated strip coupled to the chin cup.

7. An exerciser as in claim 6 wherein the chin strap comprises an adjustment buckle.

8. An exerciser as in claim 1 and further comprising a plurality of connection points, the chin strap connectable to the first and second straps at any of the connection points.

9. An exerciser as in claim 1 wherein the chin strap is connectable to the first strap by means of a pin carried by an extremity of the chin strap and a plurality of receptacles formed in the first strap and adapted to receive the pin.

10. An exerciser as in claim 1 wherein the chin strap is connectable to the first strap by means of a plurality of pins carried by the first strap and a receptacle formed in an extremity of the chin strap and adapted to receive the pins.

* * * * *